US006695812B2

(12) United States Patent
Estrada et al.

(10) Patent No.: US 6,695,812 B2
(45) Date of Patent: *Feb. 24, 2004

(54) CATHETER WITH ENHANCED FLEXIBILITY

(75) Inventors: Edward A. Estrada, Motoazabu (JP); Mina W. B. Chow, Campbell, CA (US); Kenneth L. Wantink, Temecula, CA (US); Barbara E. Stamberg, San Jose, CA (US); Chi Le Long, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 206 days.

This patent is subject to a terminal disclaimer.

(21) Appl. No.: 10/005,025

(22) Filed: Dec. 4, 2001

(65) Prior Publication Data

US 2002/0038103 A1 Mar. 28, 2002

Related U.S. Application Data

(63) Continuation of application No. 09/724,733, filed on Nov. 28, 2000, now Pat. No. 6,344,029, which is a continuation of application No. 09/345,664, filed on Jun. 30, 1999, now Pat. No. 6,193,686.

(51) Int. Cl.[7] ............................................. A61M 29/00
(52) U.S. Cl. ............................ 604/103.09; 604/103.12; 606/194
(58) Field of Search ....................... 604/103.06, 103.05, 604/103.08, 103.12, 103.04, 103.09, 103.11, 96.01; 606/192, 194

(56) References Cited

U.S. PATENT DOCUMENTS

| | | | |
|---|---|---|---|
| 4,597,755 A | 7/1986 | Samson et al. ............... 604/96 |
| 4,994,032 A | 2/1991 | Sugiyama et al. ............. 604/96 |
| 5,176,637 A | 1/1993 | Sagae .......................... 604/96 |
| 5,195,991 A | 3/1993 | Pike ............................ 604/282 |
| 5,421,826 A | 6/1995 | Crocker et al. ................ 604/53 |
| 5,458,613 A | * 10/1995 | Gharibadeh et al. ......... 606/194 |
| 5,458,615 A | 10/1995 | Klemm et al. ............... 606/198 |
| 5,460,608 A | 10/1995 | Lodin et al. ................... 604/96 |
| 5,507,768 A | 4/1996 | Lau et al. .................... 606/198 |
| 5,549,552 A | 8/1996 | Peters et al. ................... 604/96 |
| 5,549,553 A | * 8/1996 | Ressemann et al. .......... 604/96 |
| 5,670,558 A | * 9/1997 | Onishi et al. ................ 523/112 |
| 6,036,670 A | * 3/2000 | Wijeratne et al. ............. 604/96 |
| 6,344,029 B1 | * 2/2002 | Estrada et al. ......... 604/103.09 |

* cited by examiner

Primary Examiner—Manuel Mendez
(74) Attorney, Agent, or Firm—Fulwider Patton Lee & Utecht, LLP

(57) ABSTRACT

A balloon catheter system generally having an elongated catheter shaft with enhanced flexibility to facilitate more distal advancement within a patient's body lumen. The catheter shaft has a relatively stiff proximal shaft section, a relatively flexible distal shaft section and an intermediate shaft section which provides a smooth, flexible transition between the proximal and distal shaft sections. The intermediate shaft section has an improved construction with a tubular reinforcing member secured by its proximal end to the distal extremity of the proximal shaft section and a distal end secured within the proximal end of the distal shaft section. The tubular reinforcing member preferably has an inner tubular support member which has a proximal end secured to the distal end of the proximal shaft section. Preferably, the proximal shaft section has an outer jacket which extends over the tubular reinforcing member of the intermediate shaft section. Dual lumen and concentric distal shaft sections are describes. Additionally, over-the-wire constructions are described in which the inner and outer tubular members forming part of the distal shaft section extend the length of the catheter.

6 Claims, 6 Drawing Sheets

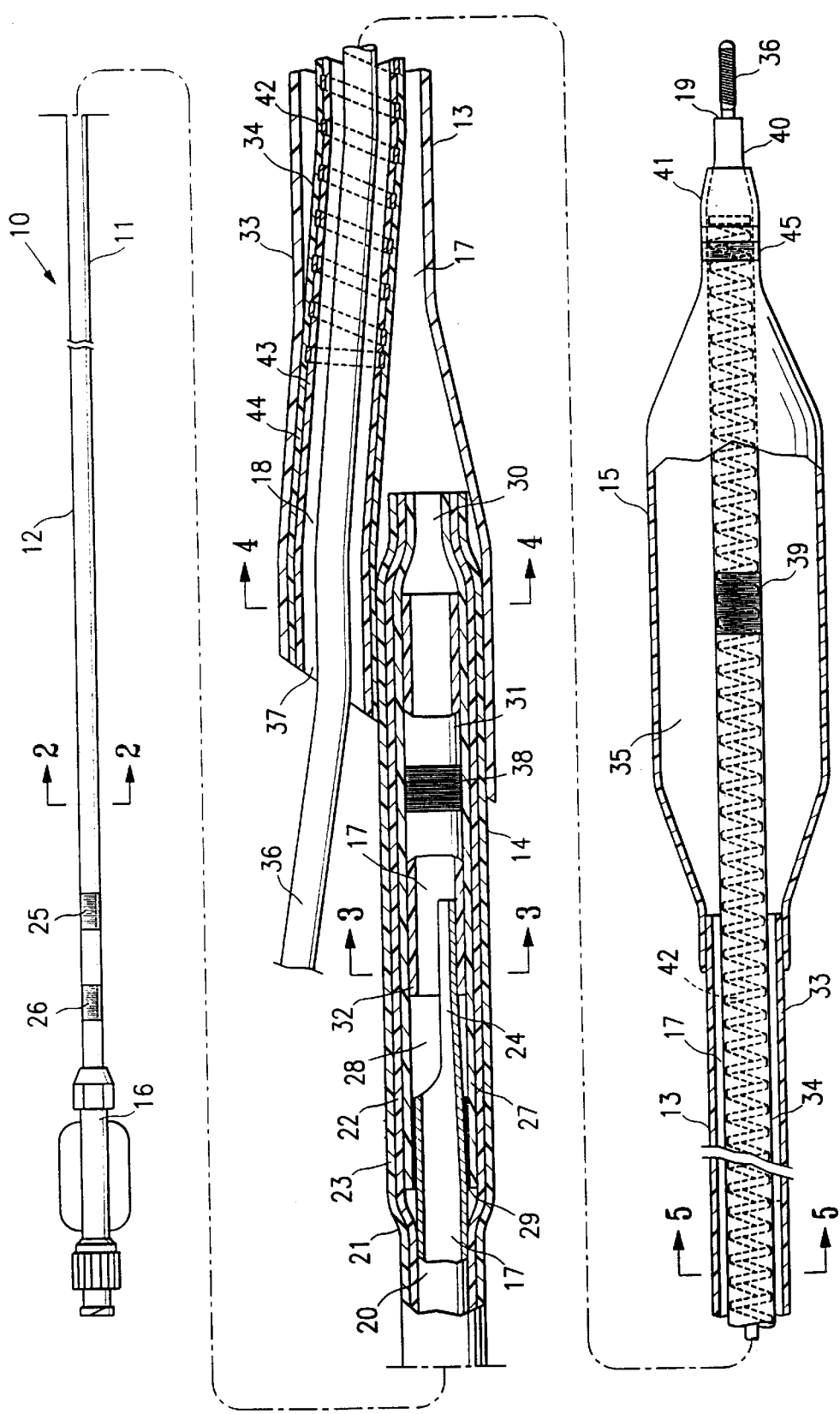

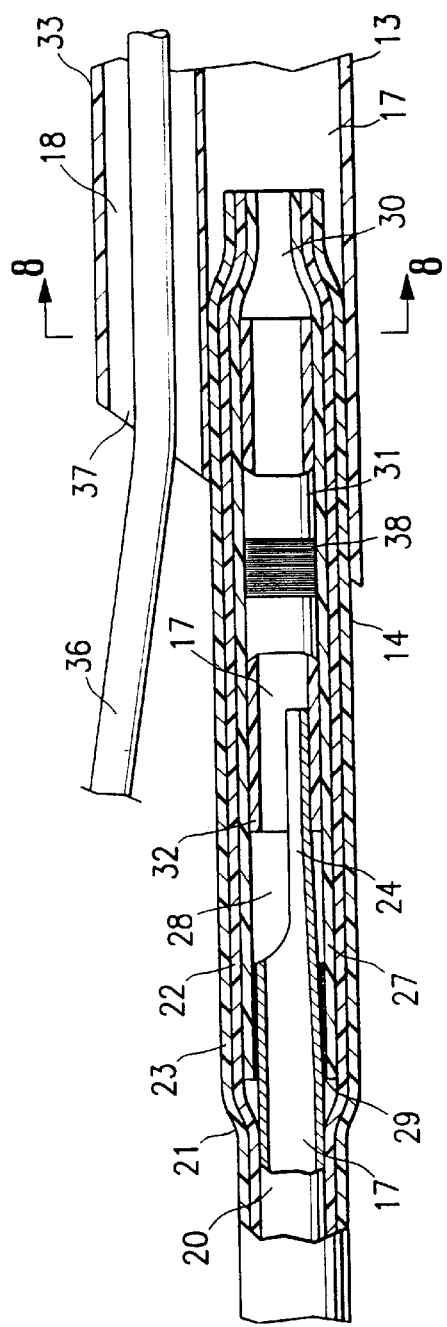
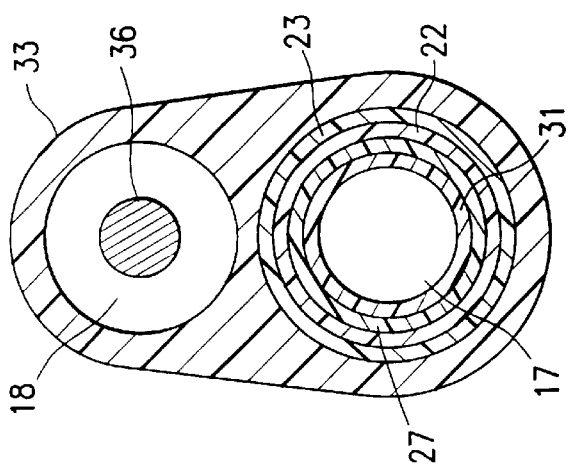
FIG. 7
FIG. 8

CATHETER WITH ENHANCED FLEXIBILITY

RELATED APPLICATIONS

This application is a continuation of copending application Ser. No. 09/724,733, filed on Nov. 28, 2000, now U.S. Pat. No. 6,344,029, which is a continuation of then copending application Ser. No. 09/345,664, filed on Jun. 30, 1999, now U.S. Pat. No. 6,193,686 B1.

BACKGROUND OF THE INVENTION

The invention relates to the field of intravascular catheters, and particularly to a catheter suitable for procedures such as angioplasty and/or stent deployment, and the like.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference. Thus, stents are used to keep open a stenosed vessel, and strengthen the dilated area by remaining inside the vessel. Instead of first using one catheter to dilate the body lumen and a second catheter to deploy the stent after the dilatation, the stent may be mounted on a balloon catheter and deployed at the same time the balloon is inflated to dilate the stenotic region.

Conventional balloon catheters for intravascular procedures, such as angioplasty and stent delivery, frequently have relatively stiff proximal shaft sections to facilitate advancement of the catheter within the patient's body lumen and a relatively flexible distal shaft sections to facilitate passage through tortuous anatomy such as distal coronary and neurological arteries without damage to the luminal wall. Typically, there is an intermediate shaft section or junction between the relatively stiff proximal shaft section and the relatively flexible distal shaft section which provides a transition between the proximal shaft section and less flexible than the distal shaft section.

A variety of intermediate shaft or junction designs have been utilized to provide a relatively smooth transition between the stiff proximal shaft section and the flexible distal shaft section. However, it has been difficult to develop a catheter design with an intermediate catheter shaft junction which provides a smooth transition and improved flexibility and which is also leak free when utilizing high pressure inflation fluid to inflate the balloon on the distal shaft section of the catheter for dilatation or stent deployment. The present invention satisfies these and other needs.

SUMMARY OF THE INVENTION

The invention is generally directed to an intraluminal catheter system with an improved transition between a proximal shaft section and a more flexible distal shaft section which greatly facilitates advancement through tortuous anatomy.

The intraluminal catheter of the invention has an elongated proximal shaft section which transitions to a more flexible distal shaft section through an improved intermediate shaft section disposed between the proximal and distal shaft sections. An inflation lumen extends within the catheter shaft to a location spaced proximal to the distal end. A guidewire receiving lumen extends within at least the distal shaft section of the catheter. The proximal shaft section has proximal and distal ends and a portion of the inflation lumen extending therein. The distal tip of the proximal shaft section is preferably tapered distally to smaller transverse dimensions. The distal shaft section has proximal and distal ends, a port in its distal end, at least part of the guidewire receiving inner lumen extending within the distal shaft section to the port in the distal end thereof, and at least part of the inflation lumen extending within the distal shaft section to a location proximal to the distal end of the distal shaft section. An inflatable member such as a balloon is preferably provided on the distal shaft section which has an interior in fluid communication with the inflation lumen.

The intermediate or transition shaft section which extends between the proximal and distal shaft sections is provided a tubular reinforcing member with proximal and distal ends, with part of the inflation lumen extending therein and with the proximal end of the tubular reinforcing member secured to the proximal shaft section proximal to the distal, preferably tapered tip. The distal end of the tubular reinforcing member extends into the inflation within the distal shaft section. An inner tubular support member may be disposed within the tubular reinforcing member with the proximal end receiving the distal tip of the proximal shaft section and secured thereto by an adhesive or other suitable means.

An outer polymeric jacket may be provided on the proximal shaft section which preferably extends distally from the proximal shaft section over the tubular reinforcing member. Preferably, the polymeric jacket extends beyond the distal end of the tubular reinforcing member into portion of the inflation lumen of the distal shaft section. The portion of the outer jacket which extends distally beyond the distal end of the tubular reinforcing member should taper to smaller transverse dimensions.

In one embodiment of the invention the distal shaft section has an outer tubular member and an inner tubular member with a portion of the inflation lumen being defined between the exterior of the inner tubular member and the interior of the outer tubular member. In this embodiment the proximal skirt of the balloon is secured to the distal end of the outer tubular member and the distal skirt of the balloon is secured to the distal extremity of the inner tubular member.

The inner tubular member extending within the distal shaft section has proximal and distal ends, ports in the proximal and distal ends and a guidewire receiving lumen extending therein between the proximal and distal ports. The proximal end of the outer tubular member surrounds and is secured to at least part of the intermediate shaft section. The inner tubular member preferably has a helical coil disposed therein, extending along a substantial length of the tubular member. A preferred construction includes the helical coil disposed within the wall of the inner tubular member and extending proximally within the inner tubular member from the distal end of the catheter to a location within the proximal extremity spaced a short distance distal to the proximal end of the inner tubular member.

This embodiment can have a rapid exchange type or over-the-wire type constructions. In the latter instance the outer tubular member and the inner tubular members extend proximally beyond the junction to the proximal end of the catheter. The inner tubular member extends along the exterior of the relatively stiff proximal portion. The outer tubular member extends to the proximal end of the catheter disposed about the proximal shaft section and the proximal extension of the inner tubular member so as to secure the two members together. In this specific embodiment, the proximal shaft section need not have the outer jacket which extends over the tubular reinforcing member in the intermediate shaft section.

Alternatively, in the rapid exchange type catheter, the distal shaft can be formed at least in part of dual lumen construction with the inflation lumen and the guidewire receiving lumen extending side-by-side along a substantial length of the distal shaft section. In this embodiment the tubular reinforcing member of the intermediate shaft section extends into the inflation lumen and secured therein. This embodiment is otherwise similar in construction to the first described embodiment above.

The tapered distal end of the proximal shaft section is preferably secured within the proximal end of the tubular reinforcing member of the intermediate shaft section. The portion of the outer tubular member which extends proximally from the proximal end of the tubular reinforcing member completes the fluid communication between the inflation lumen of the proximal shaft section with the inner lumen of the tubular reinforcing member and the portion of the inflation lumen in the distal shaft section. This construction provides enhanced flexibility to the junction between the proximal and distal shaft sections and prevents the tapered distal tip from traumatically engaging the lining of the body lumen through which the catheter passes. This embodiment may include a proximal portion of the distal shaft section with a dual lumen type construction and a distal portion of a concentric type construction with an inner tubular member and an outer tubular member as previously described.

The proximal shaft section is relatively stiff and preferably is formed from a metallic material such as stainless steel, NITINOL, MP35N, Elgiloy or other suitable high strength materials from which small diameter tubing can be readily formed. The intermediate shaft section is of intermediate stiffness and the components are formed of high strength polymeric materials such as PEEK, polyimide and the like. The outer tubular member of the distal shaft section is formed of a lower strength polymeric material such as high density polyethylene, polyamide or the like. The inner tubular member of the distal shaft section is formed from a lubricious material such as high density polyethylene and the helical coil within the inner tubular member is formed of conventional metallic materials such as stainless steel and radiopaque metals such as platinum, tantalum and alloys thereof. The inner tubular member may be of multilayered construction with the helical coil disposed between the layers.

The catheter of the present invention provides an improved design with superior pushability in the proximal shaft section, a greater degree of flexibility in the distal shaft section for more distal advancement of the catheter and an intermediate shaft section with a smoother, more flexible transition between the proximal and distal shaft sections.

These and other advantages of the invention will become more apparent from the following detailed description of the invention and the accompanying exemplary drawings.

BRIEF DESCRIPTION OF THE DRAWINGS

FIG. 1 is a schematic, elevational view partially in section of the catheter system embodying features of the invention.

FIG. 7 is a schematic longitudinal cross sectional view of an alternative embodiment wherein the distal shaft section has a dual lumen type construction.

FIG. 8 is a transverse cross sectional view of the catheter system of FIG. 7 taken along lines 8—8.

DETAILED DESCRIPTION OF THE INVENTION

Figure 3:
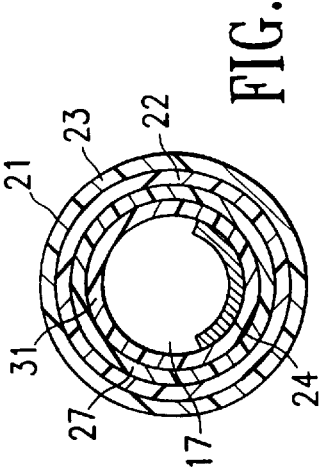
FIG. 3 is a transverse cross sectional view of the catheter system of FIG. 1 taken along lines 3—3.

FIG. 1 illustrates an intravascular catheter 10 embodying features of the invention which generally includes an elongated catheter shaft 11 with a proximal shaft section 12, a distal shaft section 13, an intermediate shaft section 14 and a radially expansive inflatable balloon 15 on the distal shaft section 13. An adapter 16 is shown mounted on the proximal end of proximal shaft section 12. An inflation lumen 17 extends within the catheter shaft 11 from the proximal end thereof to a location spaced proximal to the distal end of the shaft. A guidewire receiving lumen 18 extends within the distal shaft section 13 to port 19 in the distal end of the catheter.

Figure 2:
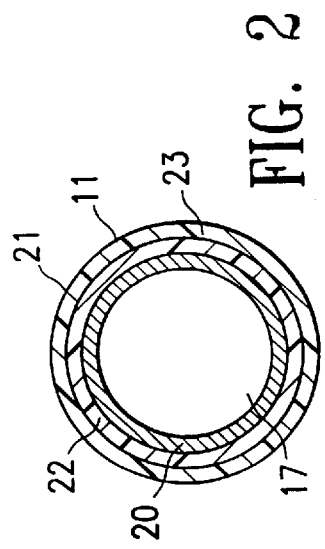
FIG. 2 is a transverse cross sectional view of the catheter system of FIG. 1 taken along lines 2—2.

The proximal shaft section 12 is formed of a high strength inner tubular member 20 with an exterior polymeric jacket 21 having inner and outer layers 22 and 23 respectively. The inflation lumen 17 within the proximal shaft section is defined by the inner tubular member 20 as shown in FIG. 2. The distal tip 24 of the inner tubular member 20 is tapered distally to smaller transverse dimensions. Brachial and femoral radiopaque markers 25 and 26 are secured to the exterior of the proximal shaft section 12 at a location distal to the adapter 16. The inner tubular member is preferably formed of 304 v stainless steel, NiTi alloy, MP35N, Elgiloy and the like. Non-metallic materials may also be used such as braided polyimide, and high strength polymers such as polyetheretherketone (PEEK), polyetherketone, polyketone. The adapter 16 and the nose piece for the adapter may be formed of conventional polymeric materials such as polycarbonate.

The intermediate shaft section 14 has a tubular reinforcing member 27 with an inner lumen 28 extending therein between the proximal port 29 and the distal port 30 in the proximal and distal ends respectively of the tubular reinforcing member. The tubular reinforcing member 27 is preferably formed of relatively high strength polymeric materials which provide the intermediate shaft section 13 with greater flexibility than the relatively more rigid proximal shaft section 12. Suitable polymeric materials include engineering polymers such as polyetheretherketone (PEEK), polyetherketone, polyketone.

The proximal extremity of the tubular reinforcing member 27 extends over and is secured to the distal extremity of the inner tubular member 20 by an adhesive proximal to the tapered distal tip 24. An inner tubular support member 31 is disposed within the inner lumen 28 of the reinforcing member 27 and preferably has the tapered distal tip 24 of the inner tubular member secured within a proximal end 32 of the inner tubular support member by a suitable adhesive such as Loctite UV 3311. Alternatively, the proximal end 32 may be fusion bonded, mechanically connected by a suitable fastener or secured by a variety of other suitable means. The jacket 21 preferably has a two layered structure, the outer layer 23 being relatively lubricious to facilitate advancement of the catheter through the lumen of a guiding catheter, other lumens and ports and the inner layer 22 being of high strength to withstand the pressures of inflation fluid. The preferred outer layer 23 is a functionalized high density polyethylene such as Plexar 209 and the preferred inner layer is polyamide such as Nylon 12.

Figure 5:
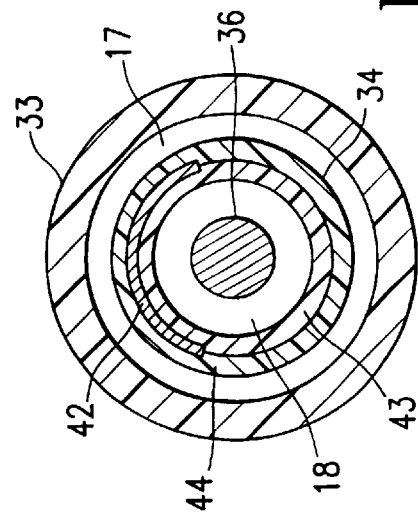
FIG. 5 is a transverse cross sectional view of the catheter system of FIG. 1 taken along lines 5—5.

The distal shaft section 13 has an outer tubular member 33 and an inner tubular member 34 disposed within the outer tubular member and defining with the outer tubular member, at least in part, the portion of the inflation lumen 17 extending within the distal shaft section. In this embodiment the inflation lumen is annular as shown in FIG. 5. The portion of the inflation lumen 17 in the distal shaft section is in fluid communication with the interior chamber 35 of the inflatable balloon 15 and with the inner lumen 28 of the tubular reinforcing member 27 of the intermediate shaft section 14.

The guidewire lumen 18 extends through the inner tubular member 34 which is configured to slidably receive a guidewire 36 suitable for advancement through a patient's body lumen such as the coronary arteries. Lumen 18 extends between distal port 19 and the proximal port 37. Notch marker 38 is provided to facilitate location of the port 37 under fluoroscopic observation. The distal extremity of the inflatable balloon 15 is sealingly secured to the distal extremity of the inner tubular member 34 and the proximal extremity of the balloon is sealingly secured to the distal extremity of the outer tubular member 33. These catheter components are preferably bonded by laser bonding which provides a flexible yet sealed bond. A mid-balloon marker 39 is provided on the exterior of the inner tubular member 34 for fluoroscopic location of the balloon during the procedure.

The distal extremity of the inner tubular member is tapered at the distal tip 40 of the catheter 10. A tapered support collar 41 formed of suitable polymeric material is disposed about the distal tip 40 distal to the distal skirt of the balloon 15 to provide a smooth entry. The collar 41 is preferably bilayered with the outer layer being relatively soft such as Pebax 55 from Elf Atochem and the inner layer being Primacor 1410 from Dow Plastics to facilitate bonding to the exterior of the inner tubular member 34.

Figure 4:
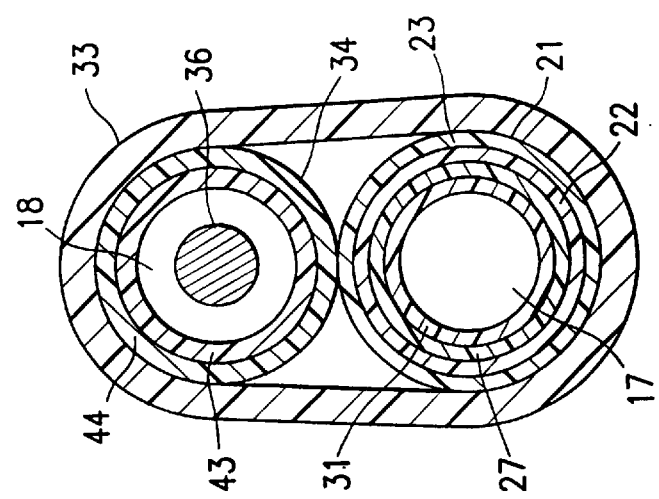
FIG. 4 is a transverse cross sectional view of the catheter system of FIG. 1 taken along lines 4—4.
Figure 6:
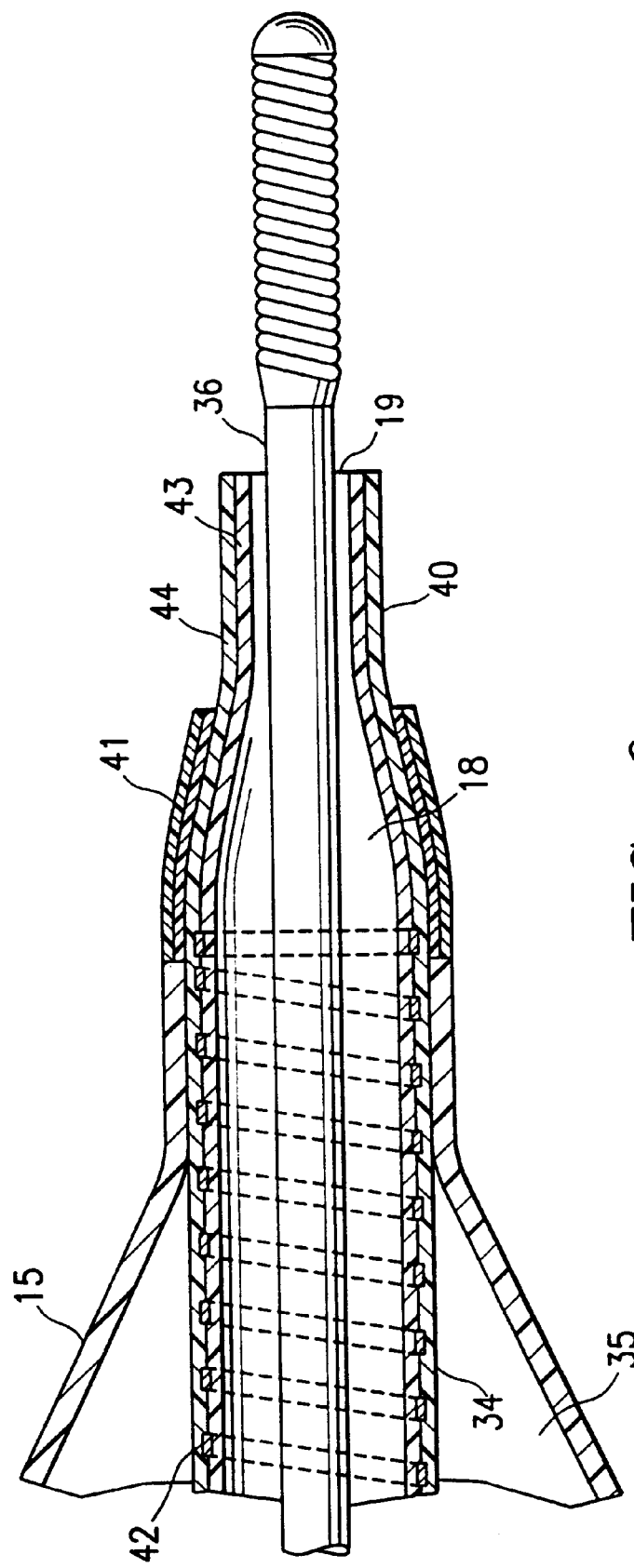
FIG. 6 is an enlarged, longitudinal cross sectional view of the inner tubular member of the catheter system of FIG. 1 within the circle 6—6.

The center section of FIG. 1 and FIG. 4 illustrate the junction between the proximal end of the distal shaft section 13 and the distal end of the intermediate shaft section 14. The proximal extremity of the outer tubular member 33 is disposed about and secured by suitable means to the jacketed tubular reinforcing member 27 and the proximal extremity of the inner tubular member 34 which is juxtaposed to the jacketed tubular reinforcing member 27. The proximal extremity of the outer tubular member 33 may be secured by heat shrinking, adhesives, fusion bonding and the like.

The inner tubular member 34 of the distal shaft section 13 preferably includes a helical coil 42 of high strength material and most preferably is a ribboned material. The coil 42 is disposed between two layers of polymeric material, an inner layer 43 and an outer layer 44. The inner layer 43 is preferably formed of lubricious material or have a lubricious inner surface. The presently preferred lubricious material is a high density polyethylene blended with functionalized high density polyethylene (e.g. Plexar 209 sold by Equistar Chemicals). The outer layer 44 is preferably compatible with the material of the balloon 15 and the outer tubular member 33 so that they can be readily bonded by fusion bonding. The presently preferred material is a polyamide elastomer, e.g. a polyether block amide such as PEBAX 55, blended with functionalized ethylene vinyl acetate polyethylene (e.g. Plexar 101 sold by Equitstar Chemicals). A distal marker 45 is provided to facilitate fluoroscopic observation of the distal tip 40 during the procedure.

The balloon 15 may be formed of suitable compliant, non-compliant or hybrid compliant material, including thermoplastic and thermosetting polymers depending upon the end use, e.g. dilatation, stent delivery etc. The presently preferred balloon polymeric material is a relatively compliant polyether block amide such as Pebax 70 sold by Elf Atochem. Other materials include Nylon 11 and 12 and Pebax 72. Compliant polymeric materials, i.e. compliant within the working expansion of the balloon, which provide a wingless balloon and which have substantially elastic recoil during deflation are also suitable for stent delivery work. Other desirable polymeric materials for balloon manufacture include polyurethanes such as TECOTHANE.

The catheter shaft will generally have the dimensions of conventional dilatation or stent deploying catheters. The length of the catheter 10, measured from the distal end of the adapter 16 to the distal end of the catheter may be about 90 cm to about 150 cm, and is typically about 137 cm. The outer tubular member 33 of the distal section has a length of about 15 cm to about 25 cm, typically about 20 cm, an outer diameter (OD) of about 0.025 in to about 0.045 in, preferably about 0.034–0.038 in and an inner diameter (ID) of about 0.02 to about 0.04, preferably about 0.028 to about 0.032 in. The inner tubular member 34 has a length of about 18 cm to about 40 cm, preferably about 25 to about 30 cm, an OD of about 0.02 to about 0.026 in and an ID of about 0.012 to about 0.022 in. The inner and outer tubular members may taper in the distal section to a smaller OD or ID.

The length of the balloon 15 may be about 10 mm to about 50 mm, preferably about 10 mm to about 40 mm. In an expanded state, the balloon diameter is generally about 0.5 mm to about 4.5 mm, typically about 1.5 to about 4 mm. The wall thickness will vary depending upon the burst pressure requirements and the hoop strength of the balloon material.

FIGS. 7 and 8 illustrate an alternative embodiment for the distal shaft section 14 of catheter 10 wherein the inflation lumen 17 and the guidewire lumen 18 are disposed within the distal section in a parallel, side-by-side relationship. The distal shaft section 14 shown in the figures is formed of an extruded polymeric material. However, the distal section may be formed by providing inner and outer tubular members, such as shown in the prior embodiment and fusing these member together into the structure shown in FIGS. 7 and 8. Parts which correspond to parts shown in FIGS. 1–6 are numbered the same.

Figure 9:
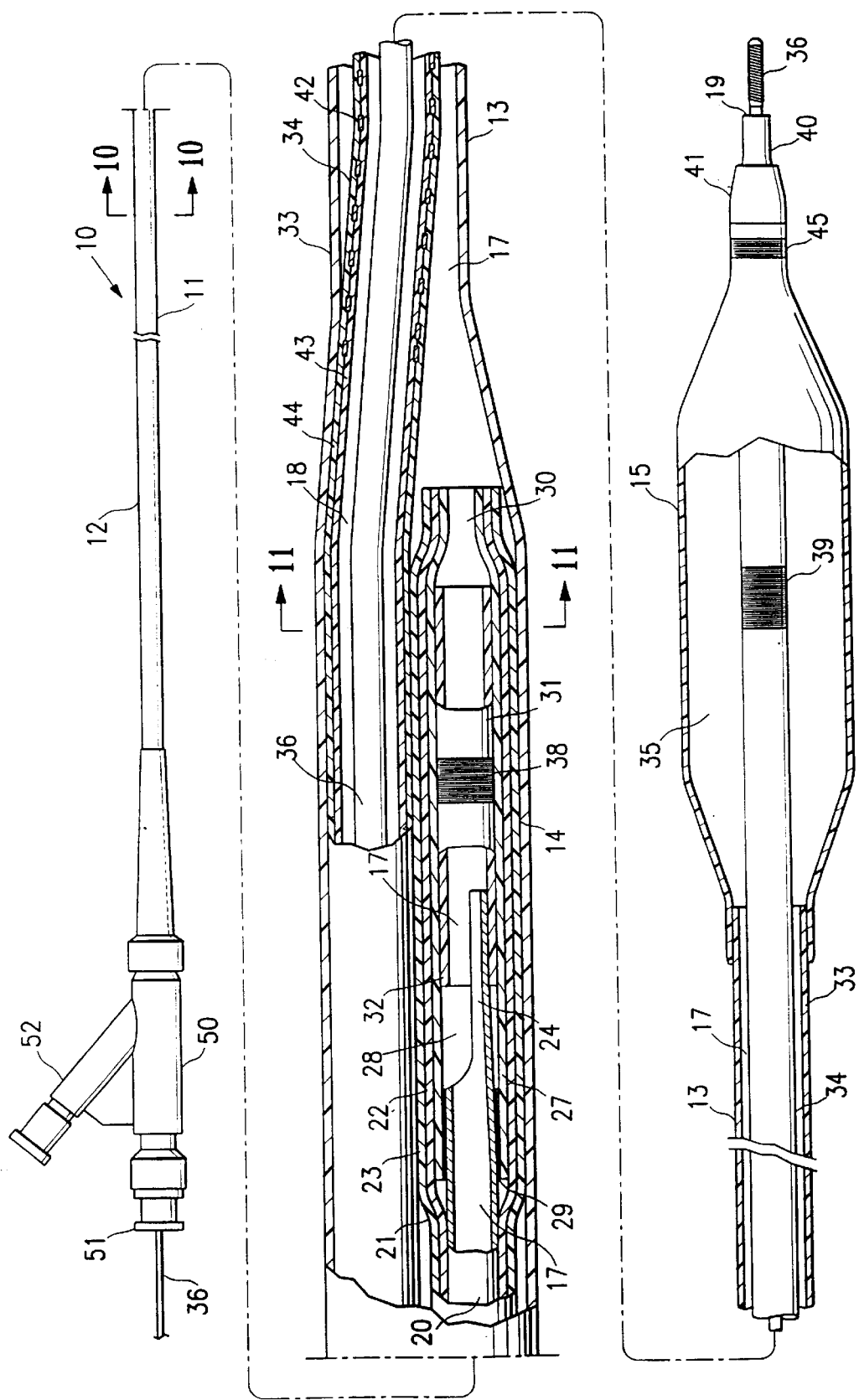
FIG. 9 is a schematic longitudinal cross sectional view of an alternative embodiment of an over-the-wire catheter having a distal shaft and intermediate shaft construction similar to that shown in FIG. 1.
Figure 11:
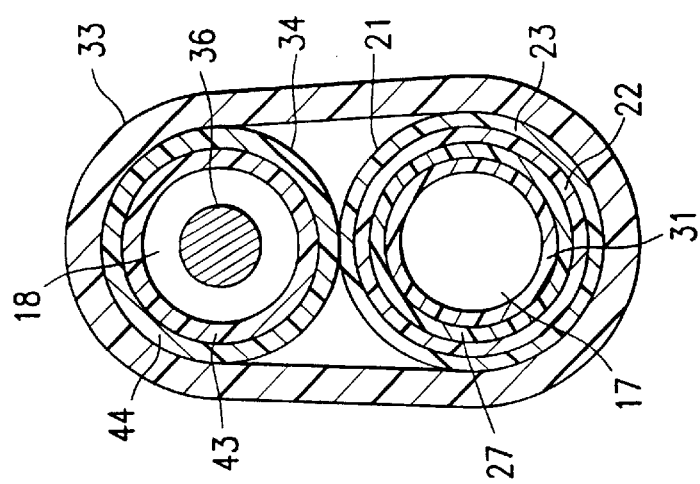
FIG. 11 is a transverse cross sectional view of the catheter system of FIG. 9 taken along lines 11—11.
Figure 10:
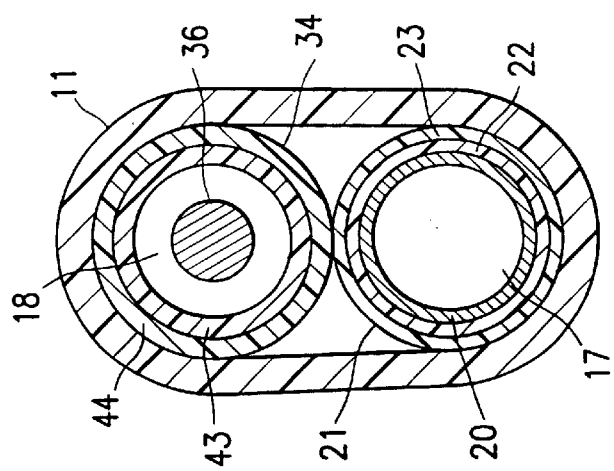
FIG. 10 is a transverse cross sectional view of the catheter system of FIG. 9 taken along lines 10—10.

FIGS. 9, 10 and 11 illustrate an over-the-wire catheter system embodying features of the invention. The catheter construction for the distal shaft section is essentially the same as that shown in FIGS. 1, 4 and 5 which has an outer tubular member 33 and an inner tubular member 34. However, in this embodiment these members extend the entire length of the catheter to provide an over-the-wire construction. Parts which correspond to the parts of the embodiment shown in FIGS. 1–6 are given the same reference number. A two arm adapter 50 is provided at the proximal end of the catheter to allow for separate communication to the guidewire lumen through arm 51 and communication to the inflation lumen through arm 52. While the outer tubular member 33 is shown in the drawings as a single member, it can comprise two or more separate sections formed of the same or different materials. As previously mentioned, the outer jacket on the inner tubular member 17 of the proximal shaft section may be deleted when the outer tubular member 33 extends over the proximal shaft section 11.

It will be apparent from the foregoing that, while particular forms of the invention have been illustrated and described, various modifications can be made without departing from the spirit and scope of the invention. Moreover, those skilled in the art will recognize that features shown in one embodiment may be utilized in other embodiments.

What is claimed is:

1. An intravascular balloon catheter comprising:
   a) an elongated shaft having proximal and distal ends, an inflation lumen extending therein and a guidewire receiving lumen extending through at least a distal portion of elongated shaft;
   b) a proximal shaft section having proximal and distal ends and a portion of the inflation lumen;
   c) a distal shaft section having a distal end, a port in the distal end, at least part of the guidewire receiving lumen extending within the distal shaft section to the port in the distal end, and at least part of the inflation lumen extending within the distal shaft section to a location proximal to the distal end of the distal shaft section;
   d) an inflatable balloon on the distal shaft section having an interior in fluid communication with the inflation lumen therein; and
   e) an intermediate shaft section extending between the proximal and distal shaft sections having a tubular reinforcing member with proximal and distal ends, with a part of the inflation lumen extending within the tubular reinforcing member and with the proximal end thereof secured to a distal extremity of the proximal shaft section proximal to the distal end thereof and the distal end of the tubular reinforcing member being secured within the inflation lumen in the distal shaft section.

2. An intravascular balloon catheter comprising:
   a. an elongated shaft having an inflation lumen extending therein and a guidewire receiving lumen;
   b. a proximal shaft section having a proximal and distal ends and an inner lumen defining part of the inflation lumen;
   c. a distal shaft section having a first tubular member with a first inner lumen forming part of the guidewire receiving lumen, a second tubular member disposed about the first tubular member along a length thereof, an inflatable balloon disposed about the first inner tubular member having a distal balloon shaft section secured to the first tubular member and a proximal balloon shaft section secured to the second tubular member, a distal tip softer than adjacent portion of the inner tubular member extending out of the distal balloon shaft section and an interior in fluid communication with the inflation lumen, a port in the distal tip of the distal shaft section in communication with the guidewire receiving inner lumen of the first inner tubular member; and
   d. a support collar disposed about and secured to the portion of the inner tubular member extending out of the distal balloon shaft section and the distal tip.

3. The intravascular catheter of claim 2 wherein the support collar has multiple layers.

4. The intravascular catheter of claim 2 wherein the support collar is formed at least in part of a polyamide elastomer.

5. The intravascular catheter of claim 4 wherein the polyamide elastomer is a polyether block amide.

6. The intravascular catheter of claim 2 wherein the support collar is tapered in the distal direction to smaller transverse dimensions.

* * * * *